(12) United States Patent
Quinet et al.

(10) Patent No.: US 7,301,014 B2
(45) Date of Patent: Nov. 27, 2007

(54) NUCLEIC ACID MOLECULE ENCODING A NOVEL ESTROGEN RECEPTOR BETA VARIANT

(75) Inventors: Elaine Marie Quinet, Berwyn, PA (US); Ermei Fan, Summit, NJ (US)

(73) Assignee: Wyeth, Madison, NJ (US)

( * ) Notice: Subject to any disclaimer, the term of this patent is extended or adjusted under 35 U.S.C. 154(b) by 591 days.

(21) Appl. No.: 10/373,271

(22) Filed: Feb. 25, 2003

(65) Prior Publication Data

US 2003/0162257 A1 Aug. 28, 2003

Related U.S. Application Data

(60) Provisional application No. 60/360,428, filed on Feb. 28, 2002.

(51) Int. Cl.
| | |
|---|---|
| C07H 21/02 | (2006.01) |
| C07H 21/04 | (2006.01) |
| C12N 15/00 | (2006.01) |
| C12N 5/00 | (2006.01) |
| C12N 5/02 | (2006.01) |

(52) U.S. Cl. .................. 536/23.1; 536/23.4; 536/23.5; 536/24.1; 435/69.1; 435/320.1; 435/325

(58) Field of Classification Search ...................... None
See application file for complete search history.

(56) References Cited

U.S. PATENT DOCUMENTS

| | | | |
|---|---|---|---|
| 5,107,065 A | 4/1992 | Shewmaker et al. | |
| 5,231,020 A | 7/1993 | Jorgensen et al. | |
| 5,710,017 A * | 1/1998 | Moore et al. | 435/69.1 |
| 6,222,015 B1 * | 4/2001 | Wilkinson | 530/350 |
| 6,818,758 B2 * | 11/2004 | Kalush et al. | 536/24.3 |

FOREIGN PATENT DOCUMENTS

| | | |
|---|---|---|
| WO | WO 99/07847 A1 | 2/1999 |
| WO | WO 01/62793 A2 | 8/2001 |

OTHER PUBLICATIONS

Mahairas et al 1999. PNAS 96:9739-9744.*
Hussey, Stephen L. et al., Organic Letters, 4(3), 415-418 (2002).
Cowley, Shaun M. et al., The Journal of Biological Chemistry, 272(32), 19858-19862 (1997).
Kuiper, George G.J. et al., Proc. Natl. Acad. Sci., USA, 93, 5925-5930 (1996).
Mosselman, Sietse et al., FEBS Letters, 392, 49-53 (1996).
Bhat, Ramesh A. et al., J. Steroid Biochem. Molec. Biol., 67(3), 233-240 (1998).
Pettersson, Katarina et al., Molecular Endocrinology, 11(10), 1486-1495 (1997).
Pace, Paul et al., The Journal of Biological Chemistry, 272(41), 25832-25838 (1997).
Enmark, Eva et al., Journal of Clinical Endocrinology & Metabolism, 82(12), 4258-4265 (1997).
Lu, B. et al., Molecular & Cellular Endocrinology, 138, 199-203 (1998).
Murphy, Leigh C. et al., J. Steroid Biochem. Molec. Biol., 65(1-6), 175-180 (1998).
Murphy, Leigh C. et al., J. Steroid Biochem. Molec. Biol., 62(5/6), 363-372 (1997).
Lazennec, Gwendal et al., Molecular Endocrinology, 13(6), 969-980 (1999).
Moore, John T. et al., Biochemical & Biophysical Research Communications, 247, 75-78 (1998).
Ogawa, Sumito et al., Nucleic Acids Research, 26(15), 3505-3512 (1998).
Kastner, Ph. et al., Proc. Natl. Acad. Sci., 87, 2700-2704 (1990).
Green, Stephen et al., Nature, 320, 134-139 (1986).
Leroy, Pierre et al., The EMBO Journal, 10(I), 59-69 (1991).
Zalent, A. et al., The EMBO Journal, 10(1), 71-81 (1991).
Farhat, Michel et al., The FASEB Journal, 10, 615-624 (1996).
Sambrook et al., Molecular Cloning, A Laboratory Manual, 2$^{nd}$ Ed., 9.46-9.62 (1989).
Old, R. W. et al., Principles of Gene Manipulation, 5$^{th}$ Ed., 11-21 (1992).
Biochem. J., 219, 345-373 (1984).
Altschul, Stephen F. et al., J. Mol. Biol., 215, 403-410 (1990).
Jones, Jonathan, D.G. et al., The EMBO Journal, 4(10), 2411-2418 (1985).
Fuqua, Suzanne A.W. et al., Cancer Research, 52, 483-486 (1992).
Fuqua, Suzanne A.W. et al., Cancer Research, 51, 105-109 (1991).
Altschul, Stephen F. et al., J. Mol. Biol., 215, 403-410 (1990).
Carrillo, Humberto et al., SIAM J. Appl. Math, 48(5), 1073-1082 (1988).
Cornish-Bowden, Athel, Nucleic Acids Research, 13(9), 3021-3030 (1985).
Devereux John et al., Nucleic Acids Research, 12(1), 387-395 (1984).
Knobil, Ernst et al., The Physiology of Reproduction, Chapter I, 3-26 (1988).
Dealmeida, Elionor et al., Mol. Gen. Genet., 218, 78-86 (1989).
Miller, J.H., Gene Transfer Vectors for Mammalian Cells, pp. 1-3; 10-14; 29-45 (1987).

* cited by examiner

*Primary Examiner*—Lorraine Spector
*Assistant Examiner*—Shulamith H Shafer
(74) *Attorney, Agent, or Firm*—Wilmer Cutler Pickering Hale and Dorr LLP

(57) ABSTRACT

This invention relates to an isolated nucleotide fragment of a novel estrogen receptor, in particular, a novel ERβ variant protein and isolated nucleic acid fragment comprising the coding regions of the genes encoding such variant proteins. Also provided are vectors, host cells, and methods for producing the novel ERβ variant protein. The invention further relates to method of obtaining such nucleotide fragment and the method of determining the presence of such ERβ variant protein in a sample.

21 Claims, 10 Drawing Sheets

Inverse PCR strategy for cloning novel ERβ 3' flanking sequences from human cDNA library.

Sequencing and Preliminary Analysis of the Clone

- Exon 6 sequence identical to the human ERβ cDNA
- C-terminal 61 aa's of ERb replaced by a unique 7 aa sequence

Figure 2

Relative Abundance of ERα, ERβ and ERβcx2 Isoforms in Human Testis RNA by RT-PCR analysis.

Transactivation of ERE-tk-Luciferase reporter by estrogen receptor isoforms, ERα, ERβ, and ERβcx2.

Cells were incubated in presence( + )or absence (-) of estradiol for 48 hrs.

SEQUENCE LISTING

```
<160> NUMBER OF SEQ ID NOS: 23

<210> SEQ ID NO 1
<211> LENGTH: 555
<212> TYPE: PRT
<213> ORGANISM: human testis
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: misc_feature
<222> LOCATION: (542)..(545)
<223> OTHER INFORMATION: Xaa can be any naturally occurring amino acid

<400> SEQUENCE: 1

Lys Val Phe Ser Gln Leu Leu Ser Gln Asp Met Asn Ile Lys Asn Ser
1               5                   10                  15

Pro Ser Leu Asn Ser Pro Ser Ser Tyr Asn Cys Ser Gln Ser Ile
            20                  25                  30

Leu Pro Leu Glu His Gly Ser Ile Tyr Ile Pro Ser Ser Tyr Val Asp
        35                  40                  45

Ser His His Glu Tyr Pro Ala Met Thr Phe Tyr Ser Pro Ala Val Met
    50                  55                  60
```

-continued

```
Asn Tyr Ser Ile Pro Ser Asn Val Thr Asn Leu Gly Gly Pro Gly
 65                  70                  75                  80

Arg Gln Thr Thr Ser Pro Asn Val Leu Trp Pro Thr Pro Gly His Leu
                 85                  90                  95

Ser Pro Leu Val Val His Arg Gln Leu Ser His Leu Tyr Ala Glu Pro
            100                 105                 110

Gln Lys Ser Pro Trp Cys Glu Ala Arg Ser Leu Glu His Thr Leu Pro
        115                 120                 125

Val Asn Arg Glu Thr Leu Lys Arg Lys Val Ser Gly Asn Arg Cys Ala
    130                 135                 140

Ser Pro Val Thr Gly Pro Gly Ser Lys Arg Asp Ala His Phe Cys Ala
145                 150                 155                 160

Val Cys Ser Asp Tyr Ala Ser Gly Tyr His Tyr Gly Val Trp Ser Cys
                165                 170                 175

Glu Gly Cys Lys Ala Phe Phe Lys Arg Ser Ile Gln Gly His Asn Asp
            180                 185                 190

Tyr Ile Cys Pro Ala Thr Asn Gln Cys Thr Ile Asp Lys Asn Arg Arg
        195                 200                 205

Lys Ser Cys Gln Ala Cys Arg Leu Arg Lys Cys Tyr Glu Val Gly Met
    210                 215                 220

Val Lys Cys Gly Ser Arg Arg Glu Arg Cys Gly Tyr Arg Leu Val Arg
225                 230                 235                 240

Arg Gln Arg Ser Ala Asp Glu Gln Leu His Cys Ala Gly Lys Ala Lys
                245                 250                 255

Arg Ser Gly Gly His Ala Pro Arg Val Arg Glu Leu Leu Asp Ala
            260                 265                 270

Leu Ser Pro Glu Gln Leu Val Leu Thr Leu Leu Glu Ala Glu Pro Pro
        275                 280                 285

His Val Leu Ile Ser Arg Pro Ser Ala Pro Phe Thr Glu Ala Ser Met
    290                 295                 300

Met Met Ser Leu Thr Lys Leu Ala Asp Lys Glu Leu Val His Met Ile
305                 310                 315                 320

Ser Trp Ala Lys Lys Ile Pro Gly Phe Val Glu Leu Ser Leu Phe Asp
                325                 330                 335

Gln Val Arg Leu Leu Glu Ser Cys Trp Met Glu Val Leu Met Met Gly
            340                 345                 350

Leu Met Trp Arg Ser Ile Asp His Pro Gly Lys Leu Ile Phe Ala Pro
        355                 360                 365

Asp Leu Val Leu Asp Arg Asp Glu Gly Lys Cys Val Glu Gly Ile Leu
    370                 375                 380

Glu Ile Phe Asp Met Leu Leu Ala Thr Thr Ser Arg Phe Arg Glu Leu
385                 390                 395                 400

Lys Leu Gln His Lys Glu Tyr Leu Cys Val Lys Ala Met Ile Leu Leu
                405                 410                 415

Asn Ser Ser Met Tyr Pro Leu Val Thr Ala Thr Gln Asp Ala Asp Ser
            420                 425                 430

Ser Arg Lys Leu Ala His Leu Leu Asn Ala Val Thr Asp Ala Leu Val
        435                 440                 445

Trp Val Ile Ala Lys Ser Gly Ile Ser Ser Gln Gln Ser Met Arg
    450                 455                 460

Leu Ala Asn Leu Leu Met Leu Leu Ser His Val Arg His Ala Arg Leu
465                 470                 475                 480

Tyr Ile Trp Ala Leu Lys Met Phe Ala Ala Leu Lys Gln Ile Leu Arg
```

```
                    485                 490                 495
Pro Ala Phe Pro Ser Ser Arg Glu Cys Phe Pro Tyr Cys Val Pro Leu
                500                 505                 510
Met Ser Met Ala Leu Ser Gln Arg Val His Asp Ile Asn Lys Val Phe
            515                 520                 525
His Tyr Phe Gly Phe Xaa Lys Lys Lys Lys Lys Lys Xaa Xaa Xaa
        530                 535                 540
Xaa Lys Lys Gly Arg Pro Leu Arg Ile Pro Arg
545                 550                 555

<210> SEQ ID NO 2
<211> LENGTH: 1682
<212> TYPE: DNA
<213> ORGANISM: human testis
<220> FEATURE:
<221> NAME/KEY: misc_feature
<222> LOCATION: (1613)..(1613)
<223> OTHER INFORMATION: n is a, c, g, or t
<220> FEATURE:
<221> NAME/KEY: misc_feature
<222> LOCATION: (1638)..(1638)
<223> OTHER INFORMATION: n is a, c, g, or t
<220> FEATURE:
<221> NAME/KEY: misc_feature
<222> LOCATION: (1642)..(1642)
<223> OTHER INFORMATION: n is a, c, g, or t
<220> FEATURE:
<221> NAME/KEY: misc_feature
<222> LOCATION: (1645)..(1646)
<223> OTHER INFORMATION: n is a, c, g, or t

<400> SEQUENCE: 2
caaggtgttt tctcagctgt tatctcaaga catgaatata aaaaactcac catctagcct      60
taattctcct tcctcctaca actgcagtca atccatctta cccctggagc acggctccat    120
atacataccc tcctcctatg tagacagcca ccatgaatat ccagccatga cattctatag    180
ccctgctgtg atgaattaca gcattcccag caatgtcact aacttggaag gtgggcctgg    240
tcggcagacc acaagcccaa atgtgttgtg gccaacacct gggcaccttt ctcctttagt    300
ggtccatcgc cagttatcac atctgtatgc ggaacctcaa aagagtccct ggtgtgaagc    360
aagatcgcta gaacacacct tacctgtaaa cagagagaca ctgaaaagga aggttagtgg    420
gaaccgttgc gccagccctg ttactggtcc aggttcaaag agggatgctc acttctgcgc    480
tgtctgcagc gattacgcat cgggatatca ctatggagtc tggtcgtgtg aaggatgtaa    540
ggccttttttt aaaagaagca ttcaaggaca taatgattat atttgtccag ctacaaatca    600
gtgtacaatc gataaaaacc ggcgcaagag ctgccaggcc tgccgacttc ggaagtgtta    660
cgaagtggga atggtgaagt gtggctcccg gagagagaga tgtgggtacc gccttgtgcg    720
agacagaga agtgccgacg agcagctgca ctgtgccggc aaggccaaga gaagtggcgg    780
ccacgcgccc cgagtgcggg agctgctgct ggacgccctg agcccgagc agctagtgct    840
caccctcctg gaggctgagc cgccccatgt gctgatcagc cgccccagtg cgcccttcac    900
cgaggcctcc atgatgatgt ccctgaccaa gttggccgac aaggagttgg tacacatgat    960
cagctgggcc aagaagattc ccggctttgt ggagctcagc ctgttcgacc aagtgcggct   1020
cttggagagc tgttggatgg aggtgttaat gatgggctg atgtggcgct caattgacca   1080
ccccggcaag ctcatctttg ctccagatct tgttctggac agggatgagg ggaaatgcgt   1140
agaaggaatt ctgaaatct ttgacatgct cctggcaact acttcaaggt ttcgagagtt   1200
aaaactccaa cacaaagaat atctctgtgt caaggccatg atcctgctca attccagtat   1260
```

```
gtaccctctg gtcacagcga cccaggatgc tgacagcagc cggaagctgg ctcacttgct    1320
gaacgccgtg accgatgctt tggtttgggt gattgccaag agcggcatct cctcccagca    1380
gcaatccatg cgcctggcta acctcctgat gctcctgtcc cacgtcaggc atgcgaggct    1440
ttacatttgg ccttgtaga aatgaatgtt tgctgctctg tgaaagcaga ttttgagacc    1500
tgctttccct tcctccaggg agtgttttcc ttactgtgtc cctttaatgt ctatggcact    1560
gtcgcagaga gtttaacatg atataaataa agtgtttcat tattttggct ttnaaaaaaa    1620
aaaaaaaaaa aaaaaanaa anaannaaaa aaaagggcgg ccgctctaga ggatccctcg    1680
ag                                                                  1682

<210> SEQ ID NO 3
<211> LENGTH: 7
<212> TYPE: PRT
<213> ORGANISM: fetal brain

<400> SEQUENCE: 3

Arg Leu Tyr Ile Trp Ala Leu
1               5

<210> SEQ ID NO 4
<211> LENGTH: 245
<212> TYPE: DNA
<213> ORGANISM: fetal brain
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (208)..(209)
<223> OTHER INFORMATION: n is a, c, g, or t

<400> SEQUENCE: 4
gctttacatt tgggccttgt agaaatgaat gtttgctgct ctgtgaaagc agattttgag     60
acctgctttc ccttcctcca gggagtgttt tccttactgt gtccctttaa tgtctatggc    120
actgtcgcag agagtttaac atgatataaa taaagtgttt cattattttg gctttnaaaa    180
aaaaaaaaaa aaaaaaaaaa naaanaanna aaaaaagggg cggccgctct agaggatccc    240
tcgag                                                               245

<210> SEQ ID NO 5
<211> LENGTH: 25
<212> TYPE: DNA
<213> ORGANISM: artificial sequence
<220> FEATURE:
<223> OTHER INFORMATION: primer sequence

<400> SEQUENCE: 5
gctcagcctg ttcgaccaag tgcgg                                          25

<210> SEQ ID NO 6
<211> LENGTH: 25
<212> TYPE: DNA
<213> ORGANISM: artificial sequence
```

```
<220> FEATURE:
<223> OTHER INFORMATION: primer sequence

<400> SEQUENCE: 6
cacaaagccg ggaatcttct tggcc                                          25

<210> SEQ ID NO 7
<211> LENGTH: 24
<212> TYPE: DNA
<213> ORGANISM: artificial sequence
<220> FEATURE:
<223> OTHER INFORMATION: primer sequence

<400> SEQUENCE: 7
gaagctggct cacttgctga acgc                                           24

<210> SEQ ID NO 8
<211> LENGTH: 25
<212> TYPE: DNA
<213> ORGANISM: artificial sequence
<220> FEATURE:
<223> OTHER INFORMATION: primer sequence

<400> SEQUENCE: 8
taatacgact cactataggg agaga                                          25

<210> SEQ ID NO 9
<211> LENGTH: 24
<212> TYPE: DNA
<213> ORGANISM: artificial sequence
<220> FEATURE:
<223> OTHER INFORMATION: primer sequence

<400> SEQUENCE: 9
tatgacgtcg catgcacgcg taag                                           24

<210> SEQ ID NO 10
<211> LENGTH: 35
<212> TYPE: DNA
<213> ORGANISM: artificial sequence
<220> FEATURE:
<223> OTHER INFORMATION: primer sequence

<400> SEQUENCE: 10
caaggtgttt tctcagctgt tatctcaaga catgg                               35

<210> SEQ ID NO 11
<211> LENGTH: 26
<212> TYPE: DNA
<213> ORGANISM: artificial sequence
<220> FEATURE:
<223> OTHER INFORMATION: primer sequence

<400> SEQUENCE: 11
ccaaatgtaa agcctcgcat gcctga                                         26

<210> SEQ ID NO 12
<211> LENGTH: 26
<212> TYPE: DNA
<213> ORGANISM: artificial sequence
<220> FEATURE:
<223> OTHER INFORMATION: primer sequence

<400> SEQUENCE: 12
acaagggcat ggaacatctg ctcaac                                         26
```

<210> SEQ ID NO 13
<211> LENGTH: 24
<212> TYPE: DNA
<213> ORGANISM: artificial sequence
<220> FEATURE:
<223> OTHER INFORMATION: primer sequence

<400> SEQUENCE: 13
ctgagactgt gggttctggg agcc                24

<210> SEQ ID NO 14
<211> LENGTH: 23
<212> TYPE: DNA
<213> ORGANISM: artificial sequence
<220> FEATURE:
<223> OTHER INFORMATION: primer sequence

<400> SEQUENCE: 14
gctttacatt tgggccttgt aga                 23

<210> SEQ ID NO 15
<211> LENGTH: 24
<212> TYPE: DNA
<213> ORGANISM: artificial sequence
<220> FEATURE:
<223> OTHER INFORMATION: primer sequence

<400> SEQUENCE: 15
aactctctgc gacagtgcca taga                24

<210> SEQ ID NO 16
<211> LENGTH: 30
<212> TYPE: DNA
<213> ORGANISM: artificial sequence
<220> FEATURE:
<223> OTHER INFORMATION: primer sequence

<400> SEQUENCE: 16
cgaggtctta ctagcaaaaa ccagtcttgg           30

<210> SEQ ID NO 17
<211> LENGTH: 29
<212> TYPE: DNA
<213> ORGANISM: artificial sequence
<220> FEATURE:
<223> OTHER INFORMATION: primer sequence

<400> SEQUENCE: 17
cagagcagca aacattcatt tctacaagg            29

<210> SEQ ID NO 18
<211> LENGTH: 22
<212> TYPE: DNA
<213> ORGANISM: artificial sequence
<220> FEATURE:
<223> OTHER INFORMATION: primer sequence

<400> SEQUENCE: 18
catctgggat ggccctactg ca                  22

<210> SEQ ID NO 19
<211> LENGTH: 29
<212> TYPE: DNA
<213> ORGANISM: artificial sequence
<220> FEATURE:
<223> OTHER INFORMATION: primer sequence

```
<400> SEQUENCE: 19
catacttccc ttgtcattgg tactggcca                                    29

<210> SEQ ID NO 20
<211> LENGTH: 21
<212> TYPE: DNA
<213> ORGANISM: artificial sequence
<220> FEATURE:
<223> OTHER INFORMATION: primer sequence

<400> SEQUENCE: 20
aacttggaag gtgggcctgg t                                            21

<210> SEQ ID NO 21
<211> LENGTH: 28
<212> TYPE: DNA
<213> ORGANISM: artificial sequence
<220> FEATURE:
<223> OTHER INFORMATION: primer sequence

<400> SEQUENCE: 21
accattccca cttcgtaaca cttccgaa                                     28

<210> SEQ ID NO 22
<211> LENGTH: 20
<212> TYPE: DNA
<213> ORGANISM: artificial sequence
<220> FEATURE:
<223> OTHER INFORMATION: primer sequence

<400> SEQUENCE: 22
cagcctgttc gaccaagtgc                                              20

<210> SEQ ID NO 23
<211> LENGTH: 29
<212> TYPE: DNA
<213> ORGANISM: artificial sequence
<220> FEATURE:
<223> OTHER INFORMATION: primer sequence

<400> SEQUENCE: 23
gttaaactct ctgcgacagt gccatagac                                    29
```

NUCLEIC ACID MOLECULE ENCODING A NOVEL ESTROGEN RECEPTOR BETA VARIANT

FIELD OF THE INVENTION

This invention is in the field of molecular biology. More specifically, this invention pertains to a newly identified polynucleotide encoding a novel estrogen receptor beta variant, and polypeptide encoded by such polynucleotide, are potentially useful in therapeutic modulation of pathophysiologic estrogen signaling.

BACKGROUND OF THE INVENTION

Estrogens are major regulators of many physiological functions, such as those associated with reproduction and mammary gland development (George et al. The physiology of Reproduction, 1988; Vol. I, page 3., Raven Press, New York). Estrogens influence growth, differentiation, and function of many target tissues including tissues of female and male reproductive tract. Estrogens also play an important role in the maintenance of bone mass and in the cardiovascular system where estrogens have certain protective effects (Farhat et al. FASEB J. 1996; 10:615-624). The effects of estrogen are mediated in either normal cell or neoplastic target cells via an initial interaction with the estrogen receptor. Estrogen receptors (alpha (ERα) and beta (ERβ)) belong to a nuclear hormone receptor superfamily of transcription factors (Green et al. Nature 1986;320:134-139, Kuiper et al. Proc. Natl. Acad. Sci. USA. 1996;93(12):5925-30, Mosselman et al. FEBS Lett 1996 Aug. 19;392(1):49-53, Enmark et al. J. Clin. Endocrinol. Metab. 1997;82(12):4258-65, Bhat et al. J Steroid Biochem Mol Biol 1998;67(3):233-40). These receptors play a critical role in hormonal modulation of gene expression by estrogen and estrogen-like ligands. Signal transduction upon ligand-binding is dependent on characteristic sequence motifs within the receptor protein. These may include a DNA binding domain (DBD), nuclear localization signals, a ligand-binding domain (LBD) and transactivation domains, TAF-1 and TAF-2 which activate transcription of target genes in a ligand independent or dependent fashion respectively. Estrogen receptors dimerize upon ligand activation and this process precipitates DNA binding (Cowley et al. J Biol Chem 1997 Aug. 8;272(32): 19858-62, Pettersson et al. Mol. Endocrinol. 1997; Sep. 11(10):1486-96, Pace et al. J. Biol. Chem. 1997;272(41):2, 5832-8). Ligand-bound receptor recognizes specific estrogen response elements within the promoter regions of estrogen-regulated genes to induce the transactivation response.

It has been shown that members of the estrogen receptor (ER) superfamily have multiple subtypes and isoforms. ER-like mRNAs distinct from the wild-type ER mRNA have been identified in many known ER positive tissues and cell lines. These isoforms have been mostly derived from alternative splicing of ER mRNAs (Lu et al. Mol Cell Endocrinol. 1998 Mar. 16;138 (1-2):199-203, (Murphy et al., J. Steroid Biochem. Mol. Bio. 1998; 65:175-180, Lu et al., Mol. Cell. Endrocrinol. 1998; 16: 199-203, Murphy et al., J. Steroid Biochem. Mol. Bio. 1997; 62: 363-372). Furthermore, there has been strong evidence that some variant/mutant ER mRNAs are stably translated in vivo and that they may have functional role(s) possibly in ER signal transduction (Fuqua et al., Cancer Research, 1992; 52, 483-486, Fuqua et al., Cancer Research, 1991; 51, 105-109). Recently several isoforms of the human ERβ gene have been described (WO 99/07847, Kastner et al. Proc. Natl. Acad. Sci. USA, 1997; 87, 2700-2704, Leroy et al. EMBO J. 10, 59-69, 1991, Zelent et al. EMBO J. 10, 71-81, 1991). Accordingly, these variant ER mRNAs produce novel proteins which differ structurally and exhibit altered physiological functions. For example, some of ER variant receptors possess anomalous transcriptional activity that may inhibit or enhance the effects of the wild-type receptors. In addition, some may act as dominant negative receptors. In one example, adenoviral delivery of a dominant negative ER to ER-positive breast cancer cells effectively suppressed estrogen-stimulated cell proliferation and the hormonal induction of endogenous genes (Lazennec et al. Mol Endocrinol. 1999; 13(6):969-80.). In another example, five transcripts arise from the human estrogen receptor β (ERβ) (Moore et al. Biochem Biophys Res Commun 1998; 247(1):75-8). In this case, full-length variants showed reduced affinity for estrogens and were able to form DNA-binding homodimers and heterodimers with each other and with the ERβ subtype. In another example, the sequence of a splice variant receptor, named ERβcx for c-terminal exchange, diverged at exon 7 (Ogawa et al. Nucleic Acids Res. 1998; 26(15):3505-12). In this case, 61 amino acids of wild-type protein sequence were substituted with a unique sequence encoding 26 amino acids. In transcription assays, the relative expression of this novel receptor had profound effects on estrogen-induced trans-activation. The evidence suggested that these effects were mediated through a heterodimerization mechanism. This isoform was shown to preferentially form heterodimers with ERα and was demonstrated to behave in a dominant negative fashion against ERα transactivation in vitro in cotransfection studies. ERβcx was shown therefore to be a potential inhibitor of estrogen (E2) action through specific interaction with the ERα isoform (Nucleic Acids Res. 1998; 26(15):3505-12).

In summary, ongoing research suggests that there exists complexity in estrogen signaling pathways and ER variants may contribute to estrogen pharmacology differently.

In order to understand the mechanism of estrogen action and ERβ regulation of gene transcription, it is important to isolate and characterize novel subtypes, variants, and/or isoforms of the ER. Once the underlying ER subtype, variant or isoform responsible for a particular disease state or pathological condition is determined, one may have a more accurate means of prognosticating the estrogen receptor related disease outcome; one may use the presence or amount of expression of the novel polynucleotide of the present invention and/or the polypeptide encoded by such polynucleotide for diagnosing associated pathological conditions or a susceptibility to an associated pathological condition; one may accurately follow therapies, develop gene specific and isoform specific therapies influenced by ER, and/or may develop new pharmaceutical drug targets.

Thus, there exists a need to identify new variants and isoforms and their protein products for the therapeutic treatment of human diseases. The present invention satisfies this need and provides related advantages as well.

SUMMARY OF THE INVENTION

The present invention provides an isolated nucleic acid fragment encoding an estrogen receptor variant polypeptide selected from the group consisting of: (a) an isolated nucleic acid fragment encoding SEQ ID NO:1; (b) an isolated nucleic acid fragment encoding an amino acid sequence having at least 95% identity with the SEQ ID NO:1; (c) an isolated nucleic acid molecule that hybridizes with the isolated nucleic acid fragment of (a) under hybridization conditions of 6×SSC (1M NaCl), 45 to 50% formamide, 1% SDS at 37° C., and a wash in 0.5× to 1×SSC at 55 to 60° C., (d) an isolated nucleic acid fragment that is complementary to (a), (b) or (c).

In an alternate embodiment, the present invention provides polypeptides encoded by the nucleotide sequences described above. It is preferred that the polypeptide of the claimed invention is involved in estrogen signaling pathway.

The invention further provides chimeric constructs comprising the isolated nucleic acid fragment of present invention operatively linked to suitable regulatory sequences.

Additionally, the invention provides a host cell comprising a chimeric construct of the present invention or an isolated nucleic acid fragment of the present invention.

In another embodiment, the invention provides for a vector comprising the isolated nucleic acid fragment of the present invention.

Additionally, the present invention provides a host cell comprising a vector of the present invention.

In an alternate embodiment, the present invention provides an isolated nucleic acid fragment selected from the group consisting of: (a) an isolated nucleic acid fragment encoding SEQ ID NO:11; an isolated nucleic acid molecule that hybridizes with the isolated nucleic acid fragment of (a) under hybridization conditions of 6×SSC (1M NaCl), 45 to 50% formamide, 1% SDS at 37° C., and a wash in 0.5× to 1×SSC at 55 to 60° C.; and (c) an isolated nucleic acid fragment that is complementary to (a), or (b).

In another embodiment, the present invention provides a method for obtaining a nucleic acid fragment encoding the polypeptide of present invention, the method comprising: (a) probing a genomic library with all or a portion of a nucleic acid fragment as set forth in SEQ ID NO:2; (b) identifying a DNA clone that hybridizes with the nucleic acid fragment of step (a); and (c) determining the sequence of the nucleic acid fragment that comprises the DNA clone identified in step (b).

In another embodiment, the present invention provides a method of detecting the presence of a nucleic acid fragment of present invention in a sample, the method comprising: (a) contacting said sample with the oligonucleotide of claim 29; and (b) determining whether the oligonucleotide detects the nucleic acid fragment.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 2 shows the nucleotide sequence and predicted amino acid composition of ERβcx2 clone isolated from a fetal brain cDNA library (referred to in Example 2).

Figure 1:
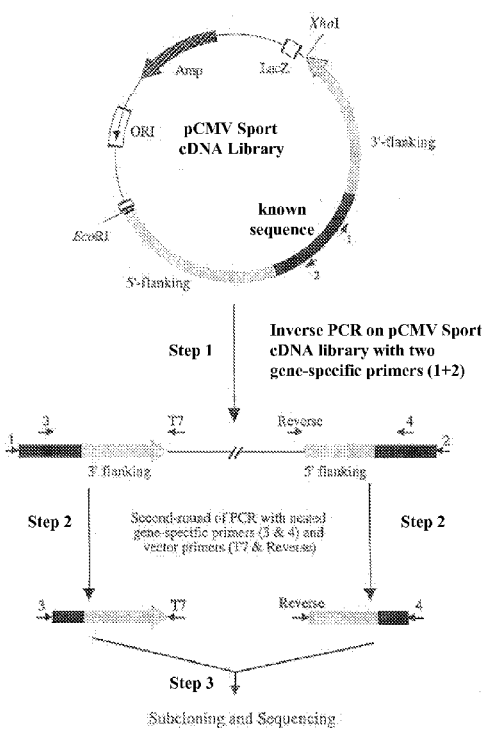
FIG. 1 depicts inverse PCR strategy for cloning novel ERβ 3' flanking sequences from human cDNA library (referred to in Example 1).

The following 23 sequence descriptions and sequence listings attached hereto comply with the rules governing nucleotide and/or amino acid sequence disclosures in patent applications as set forth in 37 C.F.R. §1.821-1.825. ("Requirements for Patent Applications containing nucleotide sequences and/or Amino Acid Sequence Disclosure—the Sequence Rules") and consistent with World Intellectual Property Organization (WIPO) Standard ST.25 (1998) and the sequence listing requirements of the EPO and PCT (Rules 5.2 and 4.95(a-bis) and Section 208 and Annex C of the Administrative Instructions). The Sequence Descriptions contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822. The present invention utilizes Lasergene software, Version 4.5, DNASTAR, Madison, Wis.

SEQ ID NO:1 is the deduced amino acid sequence of ERβcx2.

SEQ ID NO:2 is the nucleotide sequence that codes for ERβcx2.

SEQ ID NO:3 is the amino acid sequence coded by ERβcx2 exon 7.

SEQ ID NO:4 is the nucleotide sequence ERβcx2 exon 7 and 3' UTR.

SEQ ID NO:5 is the nucleotide sequence of the primer, ERβ GSP2.

SEQ ID NO:6 is the nucleotide sequence of the primer, ERβ GSP3.

SEQ ID NO:7 is the nucleotide sequence of the primer, ERβ GSP6.

SEQ ID NO:8 is the nucleotide sequence of the vector primer, T7 Sport.

SEQ ID NO:9 is the nucleotide sequence of the vector primer, Sport-forward.

SEQ ID NO:10 is the nucleotide sequence of the forward primer, GSP start 3.

SEQ ID NO:11 is the nucleotide sequence of the reverse primer, ERβ x-3.

SEQ ID NO:12 is the nucleotide sequence of the primer, GSP7-forward.

SEQ ID NO:13 is the nucleotide sequence of the primer, GSP7-reverse.

SEQ ID NO:14 is the nucleotide sequence of the primer, ERβ x-1.

SEQ ID NO:15 is the nucleotide sequence of the primer, ERβ x-2.

SEQ ID NO:16 is the nucleotide sequence of the primer, P2.

SEQ ID NO:17 is the nucleotide sequence of the primer, P3.

SEQ ID NO:18 is the nucleotide sequence of the primer, hERα-5'.

SEQ ID NO:19 is the nucleotide sequence of the primer, hERα-3'.

SEQ ID NO:20 is the nucleotide sequence of the primer, hERβ-5'.

SEQ ID NO:21 is the nucleotide sequence of the primer, hERβ-3'.

SEQ ID NO:22 is the nucleotide sequence of the primer, hERβcx2-5'.

SEQ ID NO:23 is the nucleotide sequence of the primer, hERβcx2-3'.

DETAILED DESCRIPTION OF THE INVENTION

Applicants have succeeded in identifying and characterizing a gene encoding for a novel estrogen receptor beta variant (ERβcx2). This newly identified gene produces a variant that differs structurally and functionally from the known estrogen receptor proteins. This novel human variant differs in its C-terminal sequence from the wild-type estrogen receptor in that it's C-terminal 61 amino acids are replaced by a unique sequence of 7 amino acids. Applicants have also provided evidence that this novel receptor is functional in that it interacts with the estrogen receptor and that it may act as a dominant negative mutant with inhibitory effects on the ER (e.g. ERα, ERβ) signaling pathway. The Applicants have also analyzed tissue expression of this novel variant and showed that it is most abundant in Testis.

The following definitions are provided for the full understanding of terms and abbreviations used in this specification.

The abbreviations in the specification correspond to units of measure, techniques, properties or compounds as follows: "min" means minutes, "h" means hour(s), "µL" means microliter(s), "mL" means milliliter(s), "mM" means millimolar, "M" means molar, "mmole" means millimole(s), "kb" means kilobase, "bp" means base pair(s), and "IU" means International Units.

"Polymerase chain reaction" is abbreviated PCR.

"Reverse transcriptase polymerase chain reaction" is abbreviated RT-PCR.

"Estrogen receptor" is abbreviated ER.

"DNA binding domain" is abbreviated DBD.

"Ligand binding domain" is abbreviated LBD.

"Untranslated region" is abbreviated UTR.

"Sodium dodecyl sulfate" is abbreviated SDS.

In the context of this disclosure, a number of terms shall be utilized. As used herein, the term "nucleic acid molecule" refers to the phosphate ester form of ribonucleotides (RNA molecules) or deoxyribonucleotides (DNA molecules), or any phosphoester analogs, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

The terms "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and antisense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The terms "nucleic acid" or "nucleic acid sequence" or "polynucleotide" may be used interchangeably with gene, cDNA, and mRNA encoded by a gene.

Variant(s) refer to polypeptides that differ from a reference polypeptide respectively. Generally, the differences between the polypeptide that differs in amino acid sequence from reference polypeptide, and the reference polypeptide are limited so that the amino acid sequences of the reference and the variant are closely similar overall and, in some regions, identical. A variant and reference polypeptide may differ in amino acid sequence by one or more substitutions, deletions, additions, fusions and truncations, which may be present in any combination. Additionally, a variant may be a fragment of a polypeptide of the invention that differs from a reference polypeptide sequence by being shorter than the reference sequence, such as by a terminal or internal deletion. A variant of a polypeptide of the invention also includes a polypeptide which retains essentially the same biological function or activity as such polypeptide e.g., precursor proteins which can be activated by cleavage of the precursor portion to produce an active mature polypeptide. Moreover, a variant may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide such as a leader or secretory sequence or a sequence which is employed for purification of the mature polypeptide or a precursor protein sequence. A variant of the polypeptide may also be a naturally occurring variant such as a naturally occurring allelic variant, or it may be a variant that is not known to occur naturally. Among polypeptide variants in this regard are variants that differ from the aforementioned polypeptides by amino acid substitutions, deletions or additions. The substitutions, deletions or additions may involve one or more amino acids. Alterations in the sequence of the amino acids may be conservative or non-conservative amino acid substitutions, deletions or additions. All such variants defined above are deemed to be within the scope of those skilled in the art from the teachings herein and from the art.

The ERβ variant described herein that is designated ERβcx2 (SEQ ID NO:1), is homologous to the previously known ERβ and the two genes have common N-terminal amino acid sequences corresponding to the amino acids encoded by exons 1-6 of the ERβ gene and the two genes differ in their C-terminal in that the C-terminal exon 7 sequence of the wild-type ERβ is replaced by a unique sequence of 7 amino acids. By virtue of the partial identity and partial divergence of their amino acid sequences, the variant and the known homologous may have some functionality in common but may differ in other functions. For example, wild-type ERβ is known to be a weak transcriptional activator where as ERβcx is dominant negative receptor in that it is transcriptionally inactive and that may dimerize with the ER and inactivate biological functions of the wild-type receptor.

"Dominant negative variant" refers to a variant that can act in a dominant negative fashion. Dominant negative usually is a result of a mutation creating a negative phenotype which is dominant when expressed in the presence of the wild-type protein or background. Such alterations of the nucleotide sequence encoding the ligand binding domain include but are not limited to deletions or substitutions of critical amino acid residues within the domains that are required for ligand binding. For example, dominant negative variant forms of ER (estrogen receptor) may be a result of modification of the nucleotide sequence of the ligand binding domain of the wild-type gene which would eliminate ligand binding ability of the wild-type receptor. These variants or altered forms of the estrogen receptors may be transcriptionally inactive and may suppress the biological functions of the wild-type ER, potentially by heterodimerizing with the wild-type ER.

"Splice variant" refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of them may encode different amino acid sequences. The term splice variant may also refer to the proteins encoded by the above cDNA molecules. The splice variant may be partially identical in sequence to the known homologous gene product.

"Branch site" and "3' acceptor sites" refer to consensus sequences of 3 splice junctions in eukaryotic mRNAs. Almost all introns begin with GU and end with AG (. From the analysis of many exon-intron boundaries, extended consensus sequences of preferred nucleotides at the 5 and 3 ends have been established. In addition to AG, other nucleotides just upstream of the 3 splice junction also are important for precise splicing (i.e., branch site consensus, YNYURAY and 3' acceptor site, (Y)nNAG G).

The term "polynucleotide encoding polypeptide" encompasses a polynucleotide which may include only the coding sequence as well as a polynucleotide which may include additional coding or non-coding sequence.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (Sambrook, J. et al. eds., *Molecular Cloning: A Laboratory Manual* (2d Ed. 1989) Cold Spring Harbor Laboratory Press, NY. Vols. 1-3 (ISBN 0-87969-309-6). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5× SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (Sambrook et al. eds., *Molecular Cloning: A Laboratory Manual* (2d Ed. 1989) Cold Spring Harbor Laboratory Press, NY. Vols. 1-3. (ISBN 0-87969-309-6), 9.50-9.51). For hybridization with shorter nucleic acids, i.e., oligonucleotides, the position of mismatches becomes more important, and the length of the oligonucleotide determines its specificity (Sambrook et al. eds., *Molecular Cloning: A Laboratory Manual* (2d Ed. 1989) Cold Spring Harbor Laboratory Press, NY. Vols. 1-3. (ISBN 0-87969-309-6), 11.7-11.8).

The present invention particularly contemplates nucleic acid sequences that hybridize under stringent conditions to the ERβcx2 variant coding sequences described herein and complementary sequences thereof. For the purposes of this invention, the term "stringent conditions" means hybridization will occur only if there is at least 95% and preferably at least 97% identity between the nucleic acid sequences. Accordingly, the present invention also includes isolated nucleic fragments that are complementary to the complete sequences as reported in the accompanying Sequence Listing as well as those that are at least 95% identical to such sequences, and polynucleotides having sequences that are complementary to the aforementioned polynucleotides. The polynucleotides of the present invention that hybridize to the complement of ERβcx2 variant coding sequences described herein preferably encode polypeptides that retain substantially the same biological function or activity as the mature ERβcx2 polypeptide encoded by the cDNA of SEQ ID NO:2.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computerautomated sequence comparison and identification using algorithms such as BLAST (Basic Local Alignment Search Tool; Altschul, S. F., et al., (1993) J. Mol. Biol. 215:403-410; see also www.ncbi.nlm.nih.gov/BLASTO. In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The present specification teaches partial or complete amino acid and nucleotide sequences encoding one or more particular ER variants. The skilled artisan, having the benefit of the sequences as reported herein, may now use all or a substantial portion of the disclosed sequences for purposes known to those skilled in this art. Accordingly, the present invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine.

"Identity" or "similarity", as known in the art, are relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated by known methods such as those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data*, Part I, Griffin, A. M., and Griffin, H. G., eds., Humana Press, New Jersey, 1994; and *Sequence Analysis Primer*, Gribskov, M. and Devereux, J., eds., M Stockton Press, New York, 1991. Methods commonly employed to determine identity or similarity between sequences include, but are not limited to those disclosed in Carillo, H., and Lipman, D., SIAM *J Applied Math.*, 48:1073 (1988). Methods to determine identity and similarity are codified in publicly available computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J Molec. Biol.* 215: 403 (1990)).

"Homologous" refers to the degree of sequence similarity between two polymers (i.e. polypeptide molecules or nucleic acid molecules). The homology percentage figures referred to herein reflect the maximal homology possible between the two polymers, i.e., the percent homology when the two polymers are so aligned as to have the greatest number of matched (homologous) positions.

The term "percent homology" refers to the extent of amino acid sequence identity between polypeptides. The homology between any two polypeptides is a direct function of the total number of matching amino acids at a given position in either sequence, e.g., if half of the total number of amino acids in either of the sequences are the same then the two sequences are said to exhibit 50% homology.

The term "fragment", "analog", and "derivative" when referring to the polypeptide of the present invention (SEQ ID NO:1), refers to a polypeptide which may retain essentially the same biological function or activity as such polypeptide. Thus, an analog includes a precursor protein which can be activated by cleavage of the precursor protein portion to produce an active mature polypeptide. The fragment, analog, or derivative of the polypeptide of the present invention (SEQ ID NO:1) may be one in which one or more of the amino acids are substituted with a conserved or non-conserved amino acid residue and such amino acid residue may or may not be one encoded by the genetic code, or one in which one or more of the amino acid residues includes a substituent group, or one in which the polypeptide is fused with a compound such as polyethylene glycol to increase the half life of the polypeptide, or one in which additional amino acids are fused to the polypeptide such as a signal peptide or a sequence such as polyhistidine tag which is employed for the purification of the polypeptide or the precursor protein. Such fragments, analogs, or derivatives are deemed to be within the scope of the present invention.

The polypeptide and the polynucleotides of the present invention are preferably provided in an isolated form, and preferably are purified to homogeneity.

The term "isolated" means that the material is removed from its original or native environment (e.g., the natural environment if it is naturally occurring). Therefore, a naturally-occurring polynucleotide or polypeptide present in a living animal is not isolated, but the same polynucleotide or polypeptide, separated by human intervention from some or all of the coexisting materials in the natural system, is isolated. For example, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Such polynucleotides could be part of a vector and/or such polynucleotides or polypeptides could be part of a composition, and still be isolated in that such vector or composition is not part of the environment in which it is found in nature. Similarly, the term "substantially purified" refers to a substance, which has been separated or otherwise removed, through human intervention, from the immediate chemical environment in which it occurs in Nature. Substantially purified polypeptides or nucleic acids may be obtained or produced by any of a number of techniques and procedures generally known in the field.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme.

"Codon degeneracy" refers to divergence in the genetic code permitting variation of the polynucleotide sequence without effecting the amino acid sequence of an encoded polypeptide. Accordingly, the present invention relates to any nucleic acid fragment that encodes all or a substantial portion of the amino acid sequence encoding the instant ERβcx2 protein as set forth in SEQ ID NO:1. The skilled artisan is well aware of the "codon-bias" exhibited by a specific host cell to use nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well known procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determining preferred codons can be based on a survey of genes derived from the host cell where sequence information is available.

"Gene" refers to a nucleic acid fragment that expresses a specific protein, including regulatory sequences preceding (5' noncoding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Gene control sequence" refers to the DNA sequences required to initiate gene transcription plus those required to regulate the rate at which initiation occurs. Thus a gene control sequence may consist of the promoter, where the general transcription factors and the polymerase assemble, plus all the regulatory sequences to which gene regulatory proteins bind to control the rate of these assembly processes at the promoter. For example, the control sequences that are suitable for prokaryotes may include a promoter, optionally an operator sequence, and a ribosome binding site. Eukaryotic cells are known to utilize promoters, enhancers, and/or polyadenylation signals.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein.

"Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms. Over expression of the polypeptide of the present invention may be accomplished by first constructing a chimeric gene or chimeric construct in which the coding region is operatively linked to a promoter capable of directing expression of a gene or construct in the desired tissues at the desired stage of development. For reasons of convenience, the chimeric gene or chimeric construct may comprise promoter sequences and translation leader sequences derived from the same genes. 3' Non-coding sequences encoding transcription termination signals may also be provided. The instant chimeric gene or chimeric construct may also comprise one or more introns in order to facilitate gene expression. Plasmid vectors comprising the instant chimeric gene or chimeric construct can then be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene or chimeric construct. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct."

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides include but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms.

"Clone" refers to a population of cells derived from a single cell or common ancestor by mitosis. A "cell line" refers to a clone of a primary cell that is capable of stable growth in vitro for several generations.

The present invention incorporates by reference methods and techniques well known in the field of molecular and cellular biology. These techniques include, but are not limited to techniques described in the following publications: Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4), Sambrook, J. et al. eds., *Molecular Cloning: A Laboratory Manual* (2d Ed. 1989) Cold Spring Harbor Laboratory Press, NY. Vols. 1-3. (ISBN 0-87969-309-6), Miller, J. H. & M. P. Calos eds., *Gene Transfer Vectors For Mammalian Cells* (1987) Cold Spring Harbor Laboratory Press, NY. 169 pp. (ISBN 0-87969-198-0). The DNA coding for the protein of the present invention may be any one provided that it comprises the nucleotide sequence coding for the above-mentioned protein of the present invention.

Accordingly, the present invention relates to the vectors that include polynucleotides of the present invention, host cells that genetically engineered with vectors of the present invention such as cloning vector or expression vector and to the production of polypeptides of the present invention by recombinant techniques.

The present invention further relates to a method of production of the polypeptide of the present invention by expressing a polynucleotide encoding the polypeptide of the present invention in a suitable host and recovering the expressed product employing known recombinant techniques. The polypeptide of the present invention can also be synthesized by peptide synthesizers. Host cells can be engineered with the vectors of the present invention. The host organism (recombinant host cell) may be any eukaryotic or prokaryotic cell, or multicellular organism. Suitable host cells include but are not limited to mammalian cells (e.g. such as Human hepatoma cells (HepG2), Chinese hamster ovary cells (CHO), the monkey COS-1 cell line, the mammalian cell CV-1), amphibian cells (e.g. Xenopus egg cell), yeast cells (*Saccharomyces cerevisiae, Schizosaccharomyces pombe, Pichia pastoris*), and insect cells. Furthermore, various strains of *E. coli* (e.g., DH5α, HB101, MC1061) may be used as host cells in particular for molecular biological manipulation.

The vectors may be cloning vectors or expression vectors such as in the form of a plasmid, a cosmid, or a phage or any other vector that is replicable and viable in the host cell. The engineered host cells can be cultured in conventional nutrient media modified as appropriate for activating promoters, selecting transformants or amplifying the polynucletide of the present invention. The culture conditions such as pH, temperature, and the like, are those suitable for use with the host cell selected for expression of the polynucleotide are known to the ordinarily skilled in the art.

Plasmids generally are designated herein by a lower case "p" preceded and/or followed by capital letters and/or numbers, in accordance with standard naming conventions that are familiar to those of skill in the art. The plasmids herein are either commercially available, publicly available on unrestricted bases, or can be constructed from available plasmids by routine application of well-known, published procedures. Additionally, many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The appropriate DNA sequence may be inserted into the vector by a variety of the procedures known in the art.

The DNA sequence in the expression vector may be operatively linked to an appropriate expression control sequence(s) (promoter) to direct mRNA synthesis. Such promoters include but are not limited to SV40, human cytomegalovirus (CMV) promoters (e.g. pcDNA 3.1 vector or any form of the pcDNA series), SP6, T7, and T3 RNA polymerase promoters. The expression vector may also include a ribosome binding site for translation initiation, a transcription terminator, and an appropriate sequences for amplifying the expression. The expression vector may also include one or more selectable marker genes to provide a specific phenotype for the selection of transformed host cells such as neomycin resistance for eukaryotic cells or ampicillin resistance for E. coli.

The gene may be placed under the control of a promoter, ribosome binding site (for bacterial expression), suitable gene control sequence, or regulatory sequences so that the DNA sequence encoding the protein is transcribed into RNA in the host cell transformed by a vector containing this expression construct. Such promoters include but are not limited to SV40, human cytomegalovirus (CMV) promoters (e.g. pcDNA 3.1 vector or any form of the pcDNA series), SP6, T7, and T3 RNA polymarase promoters. In some cases it may be desirable to add sequences which cause the secretion of the polypeptide from the host cell, with subsequent cleavage of the secretory signal.

It may also be desirable to reduce or eliminate expression of genes encoding the polypeptide of the present invention for some applications. In order to accomplish this, a chimeric gene or a chimeric construct designed for co-suppression of the instant polypeptide can be constructed by linking a gene or gene fragment encoding that polypeptide to a promoter sequences. Alternatively, a chimeric gene or chimeric construct designed to express antisense RNA for all or part of the instant nucleic acid fragment can be constructed by linking the gene or gene fragment in reverse orientation to a promoter sequences. Either the co-suppression or antisense chimeric genes could be introduced into desired host cell via transformation wherein expression of the corresponding endogenous genes are reduced or eliminated.

The polynucleotide of the present invention, may be in the form of RNA or in the form of DNA, which DNA includes cDNA and synthetic DNA. The DNA may be single stranded or double stranded. If it is single stranded, it may be the coding strand or non-coding (antisense) strand. The coding sequence may be identical to the coding sequence of SEQ ID NO:2 or may be a different coding sequence which the coding sequence, as a result of degeneracy or redundancy of the genetic code, encodes for the same polypeptide.

The present invention may include variants of the hereinabove described polynucleotides which encode fragments, analogs, and derivatives of the polynucleotides characterized by the deduced amino acid sequence of SEQ ID NO:1. The variant of the polynucleotide may be a naturally occurring allelic variant of the polynucleotide or a non-naturally occurring variant of the polynucleotide.

The polynucleotide of the present invention, may have a coding sequence which is a naturally occurring allelic variant of the coding sequence characterized by the DNA sequence of the SEQ ID NO:2. An Allelic variant is an alternate form of a polynucleotide sequence which which may have a substitution, deletion, or addition of one or more nucleotides, which does not substantially alter the function of the encoded polypeptide.

The polynucleotide which encodes for the mature polypeptide, i.e. ERβcx2, may include only the coding sequence for the mature polypeptide or the coding sequence for the mature polypeptide and additional sequence such as gene control sequence, regulatory or secretory sequence.

The present invention therefore includes polynucleotides wherein the coding sequence for the mature polypeptide may be operatively linked in the same reading frame to a polynucleotide sequence which aids in expression and secretion of a polypeptide from a host cell. For example, a signal peptide. The polynucleotide may also encode for a precursor protein.

The polynucleotide of the present invention may also have the coding sequence fused in frame to a marker sequence, such as hexa-histidine tag (Qiagen Inc.), at either 3' or 5' terminus of the gene to allow purification of the polypeptide of the present invention.

The polypeptide of the present invention may be produced by growing suitable host cells transformed by expression vector described above under conditions whereby the polypeptide of the interest is expressed. The polypeptide may then be isolated and purified. Methods of the purification of proteins from cell cultures are known in the art and include but not limited to ammonium sulfate precipitation, anion or cation exchange chromatography, and affinity chromatography.

Cell-free translation systems may also be employed to produce the polypeptides of the present invention using the RNAs derived from the polynucleotides of the present invention.

Large-scale production of cloned ERβcx2 would enable the screening of large numbers of ERβcx2 analogs, and would facilitate the development of new or improved agonists and antagonists in the clinical therapy of estrogen related disorders. More specifically, the screening of large numbers of analogs for ERβcx2 activity could lead to development of improved drugs for use in clinical therapy of cancer, osteoporosis, cardiovascular disorder, etc.

The novel ERβcx2 exon 7 (SEQ ID NO: 4) sequence may be used to generate a dominant negative repressor of estrogen-induced transcription. The ERβcx2 exon 7 (SEQ ID NO: 4) sequence could be incorporated into any one of the existing variants such as estrogen receptor subtypes α, β, and/or various isoforms which are generated by alternative splicing. The resulting new polypeptides comprising the amino acid sequence encoded by SEQ ID NO: 4 which is set forth in SEQ ID NO:3 may generate a dominant negative repressor of estrogen-induced transcription.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences added and/or with targeting sequences that are already present removed. While the references cited give examples of each of these, the list is not exhaustive and more targeting signals of utility may be discovered in the future.

Furthermore, the polypeptides of the present invention or cells expressing them may be used as immunogen to prepare antibodies by methods known to those skilled in the art. For example, these polypeptides encoded by SEQ ID NO: 2 or any portion of SEQ ID NO: 2 and/or encoded by SEQ ID NO:4 or cells expressing any of the aforementioned polypeptides may be used as immunogens. These antibodies can be polyclonal or monoclonal and may include chimeric, single chain, and Fab fragments or the products of the Fab expression library. The antibodies are useful for detecting the polypeptide of the present invention in situ in cells or in vitro in cell extracts.

In addition, the polypeptide of the present invention can be used as targets to facilitate design and/or identification of compounds that may be useful as drugs. In particular, these compounds may be used to treat diseases resulting from alterations in estrogen signaling pathways such as cancer, osteoporosis, cardiovascular diseases. In addition, the polypeptides of the present invention may be used to identify additional targets (e.g. co-activator or co-repressor proteins) that may influence estrogen signaling. Various uses of the ER variant of the present invention include but are not limited to therapeutic modulation of pathophysiologic estrogen signaling (e.g. gene delivery approaches, gene silencing approaches, protein therapeutics antibody therapeutics), diagnostic utility, pharmaceutical drug targets, identification of receptor-based agonists or antagonists, and study of the molecular mechanisms of estrogen action.

Accordingly, dominant negative ER variants offer utility for therapeutic modulation of pathophysiologic estrogen signaling. Estrogen-induced signaling mediated by estrogen receptors is affected by aberrant ERs. Variants may produce a constituitively active phenotype contributing to carcinogenesis or act as dominant negative modulators resulting in loss of estrogen responsiveness and rendering antiestrogen therapy ineffective. The delivery of transcriptionally altered ERs termed dominant negative mutants for example to breast cancer cells holds promise as a strategy to treat breast cancer. Furthermore, small molecules may be developed to efficiently deliver dominant negative ERs to mammalian cells circumventing the current inefficient delivery approaches and those requiring the use of recombinant virus (Hussey et al. Organic Letters 2002; 4: 4145-418). This therapeutic approach would serve as a viable alternative to the use of antiestrogens or potent competitive antagonists of estrogen receptors such as tamoxifan, particularly since most breast cancers eventually become resistant to these types of antihormone therapeutics.

Moreover, in cells refractory to antiestrogen therapy due to phenotypic expression of endogenous dominant negative ER variant of the present invention, gene-silencing approaches such as antisense, siRNA (small interfering RNA), etc might be employed as strategies to induce or stimulate estrogen signaling. Additionally, the novel variant of the present invention may be used to make fusion ER variants which may be employed toward the development of receptor-based agonists and antagonists.

The present invention relates to a novel protein, characterized in that it comprises the amino acid sequence given in SEQ ID NO:1.

In one embodiment, the invention provides polynucleotides (DNA or RNA) which encodes such a polypeptide. The nucleotide sequence of cloned PCR products were compared with existing Genbank entries using the BLAST search program. An EST clone (Genbank #AA829530) containing a larger fragment of the novel exon 7 sequence was identified. This clone of approximately 2.0 Kb was obtained (IMAGE Consortium) and sequenced. Splice acceptor consensus sites were identified using the GCG/SeqWeb program FindPatterns. In addition, the present invention provides features such as a polyadenylation signal and poly A tail as evident in the 3' UTR following the stop codon (FIG. 2). Nucleotide boundaries consistent with a consensus 5' splicing junction sequence also imply that the variant protein may be generated by alternative splicing.

In particular the invention provides a polynucleotide encoding a human ERβ variant and characterized in that it comprises the DNA sequence given in SEQ ID NO:2. The polynucleotide having the DNA sequence given in SEQ ID NO:2 was obtained from a fetal brain by conventional techniques. For example, a cDNA fragment encoding a portion of the novel ER variant was initially isolated from a fetal brain cDNA library using an inverse PCR approach (FIG. 1). Sequence analysis revealed the polypeptide as a novel human variant (FIG. 2). The novel sequence diverges at the wild-type ERβ exon 6-7 junction where the C-terminal 61 amino acids of wild-type ERβ are replaced in the variant by a unique sequence encoding 7 amino acids prior to termination as indicated.

The invention also provides a novel oligonucleotide as set forth in SEQ ID No: 11 (ERβ x-3) which spans exon 6 of the wild-type ERβ and the novel exon 7 boundary. The novel primer can act as PCR primer in the process herein described to determine whether or not the ERβcx2 gene identified whole or in part are transcribed in various tissues. The novel primer of the present invention may be used in combination with various ER primers (e.g. ERβ wild-type or ERβcx nucleotide sequence) to detect the presence of the novel variant of the present invention. It is recognized that such sequence will have utility in diagnosis of various health states which may be directly or indirectly related to the presence of this mutant from of estrogen receptor.

Figure 3:
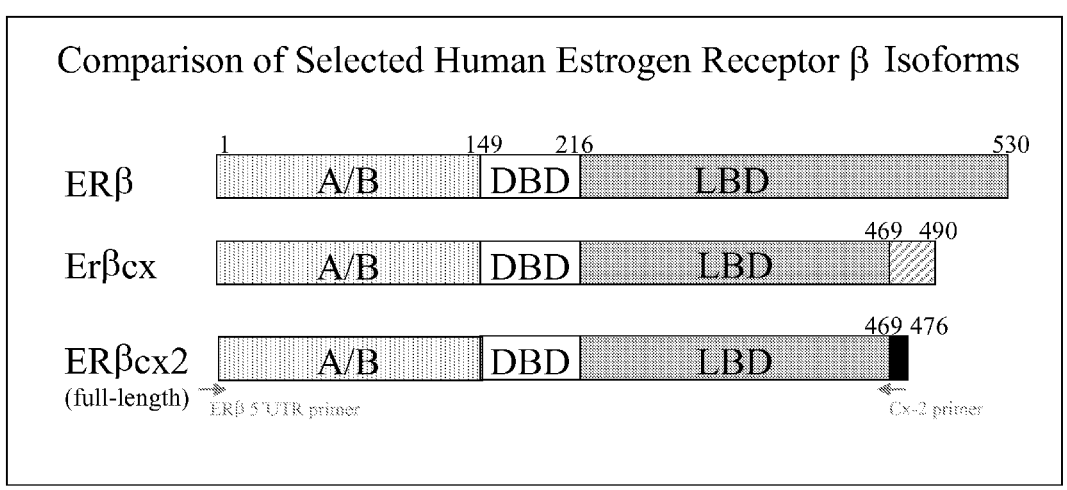
FIG. 3 shows comparison of selected human ERβ variants (referred to in Example 3).

In another embodiment, the sequence of the PCR amplified product upstream of the exon 6-7 junction was analyzed and showed almost 100% nucleotide sequence similarity with ERβ (FIG. 3). The ERβcx2 cDNA was confirmed using PCR amplification and the nucleotide sequence up to end of exon 6 is invariant with the wild-type ERβ receptor. One conservative nucleotide change was observed in the N-terminus of the amplicon, potentially a polymorphism. Adenine (A) is substituted for guanine (G) at nucleotide 35 (4th nucleotide relative to the initiation codon ATG). In the translated sequence this nucleotide change results in an amino acid substitution of aspartic acid with asparagine relative to the published ERβ sequence (D→N) or (ASP→ASN). Comparison with ERβ shows sequence identity with the A/B domain located in the N-terminus containing a transactivation function (AF-1), the DNA Binding Domain (DBD), and the hinge region. This homology however, extends to only a portion of the critical ligand binding domain (LBD), involved in binding ligand, dimerization, and transactivation.

Figure 4:
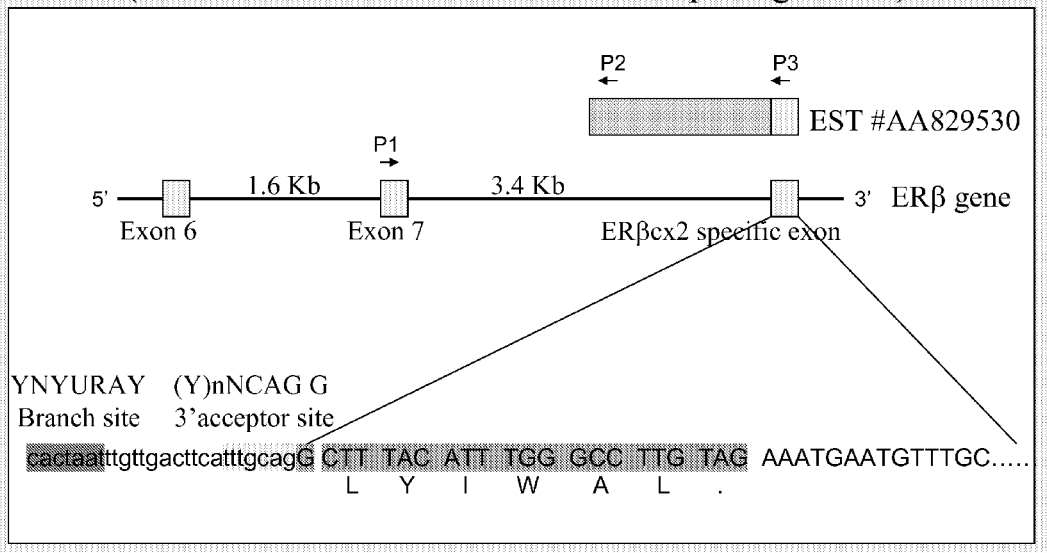
FIG. 4 shows genomic organization of ERβcx2 (referred to in Example 4).

In another embodiment, genomic organization analysis of the novel sequence confirmed that the novel ERβcx2 sequence resides about 3.4 kb downstream of ERβ exon 7 and its 3' UTR (FIG. 4). The genomic location of the novel exon 7 sequences was defined using two PAC genomic clones isolated for this purpose. Intronic consensus splicing motifs were identified upstream of the 7 amino acid coding sequence. Consensus splice signals for a branch site and 3' acceptor site, were found immediately upstream of the alternate exon 7 sequence. Therefore, the exchange of the last exon of ERβ may have been occurred by an alternative splice mechanism.

Figure 5:
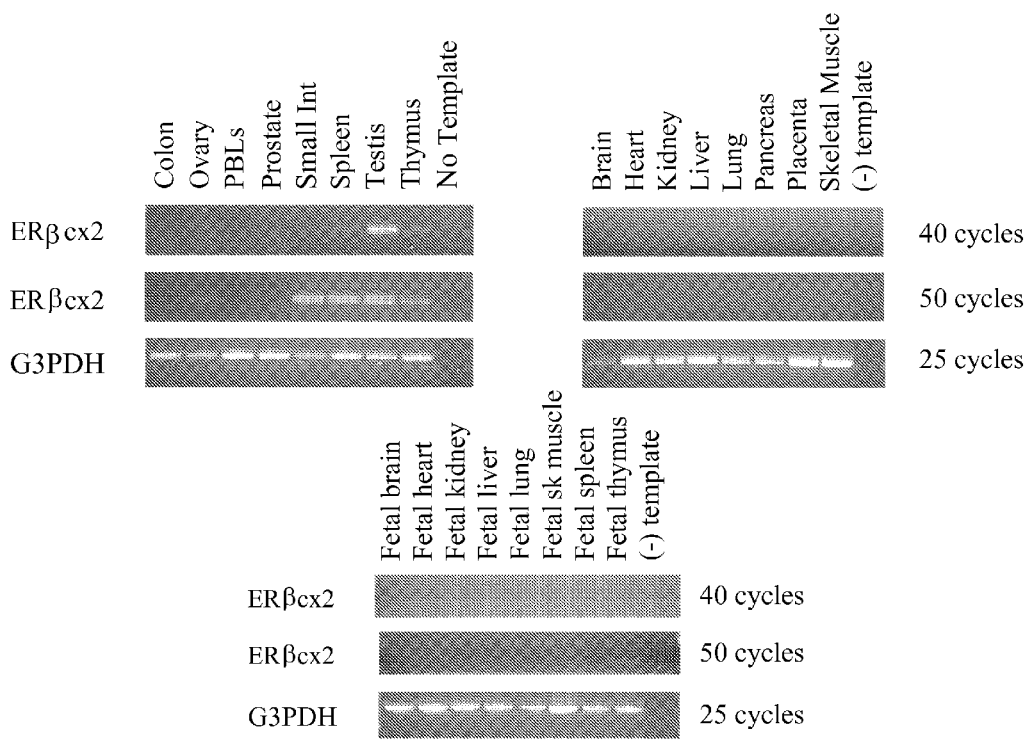
FIG. 5 shows expression of ERβcx2 transcripts in human tissues (referred to in Example 5).

In yet another embodiment, RT-PCR analysis revealed that the variant mRNA transcript of the present invention is most abundant in Testis. However, with increasing amplification cycles, expression was observed in ovary, small intestine, spleen, and thymus (FIG. 5).

Figure 6:
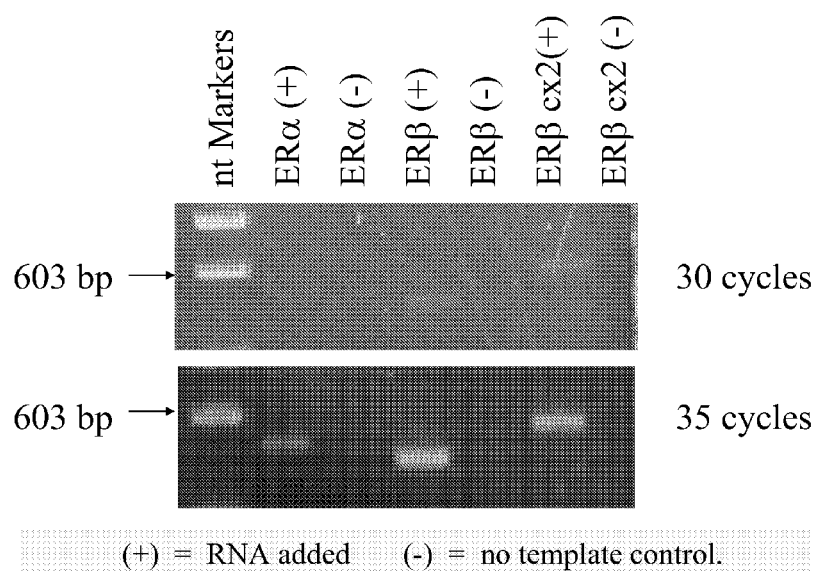
FIG. 6 shows relative abundance of ERα, ERβ and ERβcx2 variants in human testis RNA by RT-PCR analysis (referred to in Example 6).

In yet another embodiment, the relative expression of ERα, ERβ, and the novel ERβcx2 variants was determined in human testis RNA by semi quantitative RT-PCR analysis using primers specific for ERα, ERβ, and ERβcx2. The data suggest that transcripts for the novel variant are present at a comparable level to the wild-type receptors in total RNA from testis (FIG. 6). Furthermore, the expression of ERβcx2 mRNA roughly paralleled that observed for ERβcx mRNA identified in testis, ovary, prostate and thymus (Ogawa et al. Nucleic Acids Res. 1998; 26(15):3505-12). However, ERβ is predominant in thymus, testis, ovary, and spleen (Mosselman et al. FEBS Lett 1996 Aug. 19;392(1):49-53).

Figure 7:
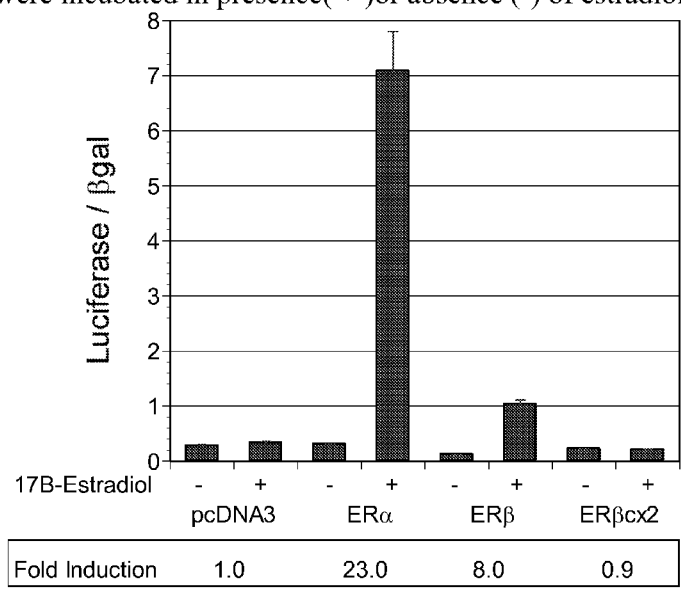
FIG. 7 shows results of transactivation of ERE-tk-Luciferase reporter by estrogen receptor variants, ERα, ERβ and ERβcx2 (referred to in Example 7).
Figure 8:
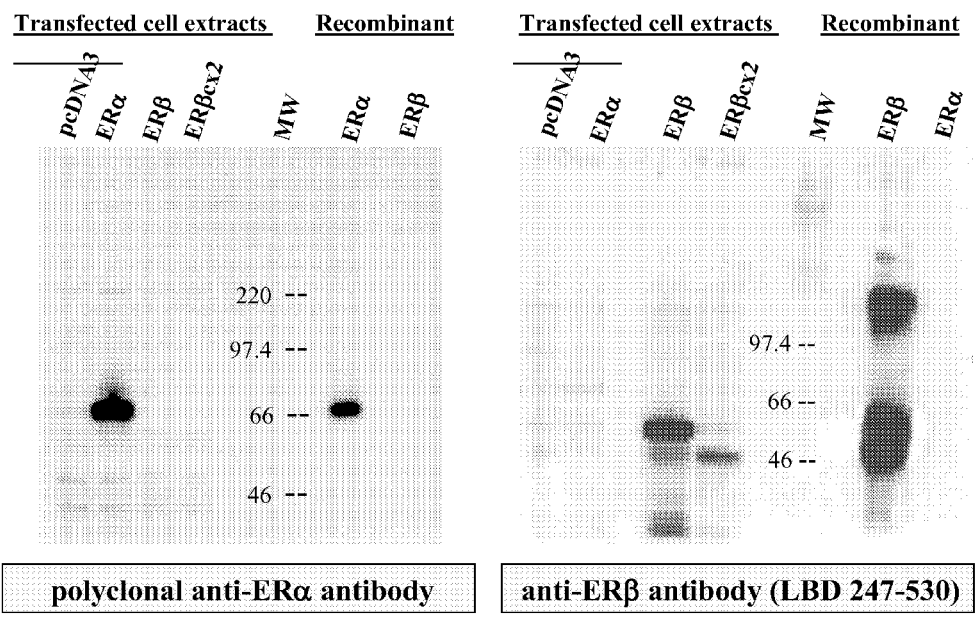
FIG. 8 shows immunoblot analysis of ERα, ERβ and ERβcx2 (referred to in Example 7).

In another embodiment, functional studies were performed to define the transactivation properties of the ERβcx2 protein (FIG. 7). Substitution of exon 7 sequences disrupts the LBD inactivating the receptor transactivation function. In transient transfection experiments, ERβcx2 was unable to induce transcription from ERE-Luciferase reporter constructs coexpressed in HepG2 cells. Immunoblot analysis of protein expression confirmed that the variant isoform, ERβcx2, was synthesized in the transfection experiments, suggesting it is nonfunctional (i.e., cannot bind ligand or transactivate) (FIG. 8).

Figure 9:
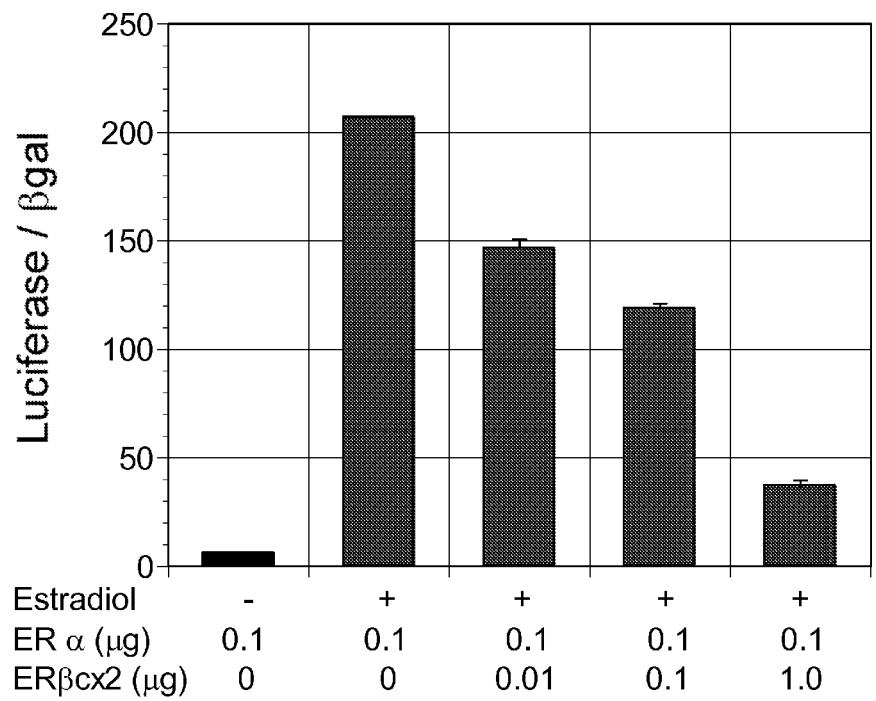
FIG. 9 shows dominant activity of ERβcx2 in the ERα signaling pathway (referred to in Example 7).
Figure 10:
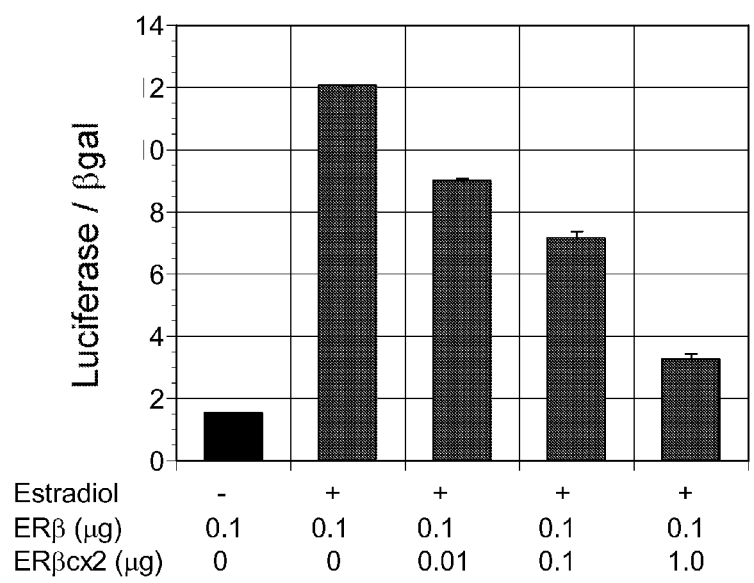
FIG. 10 shows dominant activity of ERβcx2 in the ERβ signaling pathway (referred to in Example 7).

In yet another embodiment, cotransfection experiments were performed and identified the ERβcx2 variant as a possible dominant negative mutant with inhibitory effects on the ERβ signaling pathway (ERα signaling may also be affected) (FIGS. 9 and 10).

As a naturally occurring dominant negative mutant, the novel ERβcx2 may be used for targeting of specific receptor interactions as a distinct approach in identification of tissue selective estrogen agonists and antagonists.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Cloning of Human ERβ Variant

A human fetal brain cDNA library constructed in pCMV-Sport 4.0/2.2 vector (Invitrogen, Carlsbad, Calif.), was screened for novel ERβ isoforms using a modification of an inverse PCR protocol. The primary round of inverse PCR amplification utilized two gene specific primers: ERβ GSP2: GCTCAGCCTGTTCGACCAAGTGCGG (forward) (SEQ ID NO:5), and ERβ GSP3: CACAAAGCCGGGAATCT-TCTTGGCC (reverse) (SEQ ID NO:6). Reaction conditions were those recommended by the manufacturer of the Expand™ Long Template PCR System (BMB, Indianapolis, Ind.).

A second round of PCR was performed using 1 ml of this reaction mixture in the secondary reaction containing one nested gene-specific primer, ERβ GSP6, GAAGCTGGCT-CACTTGCTGAACGC (forward) (SEQ ID NO:7) and one of the vector primers, T7-Sport: TAATACGACTCACTAT-AGGGAGAGA (SEQ ID NO:8) or Sport-forward: TAT-GACGTCGCATGCACGCGTAAG (SEQ ID NO:9) with an annealing temperature of 60° C. for 40 cycles. The resultant products were gel purified and subcloned into pCR2.1 (Invitrogen, Carlsbad, Calif.) for sequence analysis using the ABI 3700 DNA Analyzer (Applied Biosystems, Foster City, Calif.). This clone was named pERβcx2.

Example 2

Sequencing and Preliminary Analysis of the Clone

The sequence of the clone was determined as described in Example 1. The nucleotide sequence and predicted amino acid composition of pERβcx2 is shown in FIG. 2. This sequence represents one of three identical clones isolated from a fetal brain cDNA library. The N-terminal portion of the nucleotide sequence corresponds to exon 6 of the human ERβ cDNA, Genebank Accession #AB006590, AF051427, and X99101. The novel sequence diverges however at the wild-type ERβ exon 6-7 junction where the c-terminal 61 amino acids of wild-type ERβ are replaced in the variant by a unique sequence encoding 7 amino acids prior to termination as indicated.

Example 3

Isolation and Characterization of a Full-Length cDNA Clone of Novel ERβ Isoform

A full-length cDNA ERβ was isolated from testis total RNA (BD Biosciences Clontech, Palo Alto, Calif.) by RT-PCR (Pfu polymerase). The forward primer was designed to initiate directly upstream of the first ATG and the reverse primer to recognize the junction of exon 6 and the novel exon 7 sequence as indicated in FIG. 3. The forward primer, GSP start 3, CAAGGTGTTTTCTCAGCTGTTATCTCAA-GACATGG (SEQ ID NO:10) initiates upstream of the first ATG of the full-length ERβ cDNA, and the reverse primer CCAAATGTAAAGCCTCGCATGCCTGA (SEQ ID NO:11) (ERβ x-3) spans the exon 6 and unique exon 7 boundary. Two successive rounds of PCR amplification (40 cycles each) were performed with 5 μl of the first reaction mixture transferred to the second reaction. The final amplification product was cloned into bluescript SK (Stratagene, Ja Jolla, Calif.) and sequenced (FIG. 3).

Example 4

Genomic Organization

Sequence information derived from human PAC clones was used to determine the physical genomic location of the c-terminal ERβcx2 sequences relative to the human ERβ gene. Human PAC genomic clones (Genome Systems,) were identified using primers specific for exon 7 sequences in the ERβ gene (GSP7-forward ACAAGGGCATGGAACATCT-GCTCAAC (SEQ ID NO:12) and GSP7-reverse CTGAGACTGTGGGTTCTGGGAGCC (SEQ ID NO:13)). These clones were rescreened with primers specific for the novel exon 7 sequence using primers, ERβ x-1 GCTTTA-CATTTGGGCCTTGTAGA (SEQ ID NO:14) and ERβ x-2 AACTCTCTGCGACAGTGCCATAGA (SEQ ID NO:15).

The DNA isolated from the PAC clones was further characterized using a PCR strategy and sequence information derived from EST clone #AA829530. The GSP7 forward primer (P1 in FIG. 4), recognizing the wild-type ERβ exon 7 sequence was combined with reverse primers designed to amplify EST #AA829530 sequences. Reverse oligomers; P2 (CGAGGTCTTACTAGCAAAAAC-CAGTCTTGG) (SEQ ID NO:16) and P3 (CAGAGCAG-CAAACATTCATTTCTACAAGG) (SEQ ID NO:17) recognize the 5' and 3' ends of the EST sequence, respectively. Two PCR products were generated which differed in size by approximately 2 Kb; the size of the EST. The smaller product was cloned into bluescript SK (Stratagene, La Jolla, Calif.) and sequenced.

Example 5

Tissue Distribution

Tissue distribution studies were performed using PCR and Multiple Tissue cDNA panels from (MTC; BD Biosciences Clontech, Palo Alto, Calif.). PCR amplification was performed with AdvanTaq Plus DNA Polymerase reagents according to the Clontech User Manual protocol for two-step cycling. The forward primer, ERβ GSP6, GAAGCTG-GCTCACTTGCTGAACGC (SEQ ID NO:7) combined with a primer designed to the unique exon 7 nucleotide sequence, ERβ X-2, AACTCTCTGCGACAGTGC-CATAGA (SEQ ID NO:15) produces an amplicon of 278 bp. Control, G3PDH primers were used to normalize the results. A single major band of 983 bp was generated using amplification conditions recommended by the manufacturer.

The relative expression levels of ERβcx2 were determined in these tissue panels normalized for GAPDH. ERβcx2 mRNA was found to be the most abundant in testis (FIG. 5). Transcripts were also detected in ovary, small intestine, spleen, and thymus at lower concentrations and were more easily observed with increasing cycle number. A low level of ERβcx2 mRNA expression was observed in fetal thymus (FIG. 5).

Example 6

Relative Abundance of Estrogen Receptor Isoforms

RT-PCR was performed on human testis total RNA. Reverse transcription was performed with Superscript (Invitrogen, Carlsbad, Calif.). Amplification was performed by two-step PCR (denaturing at 95° C. for 30 seconds, annealing at 70° C. for 1.5 minutes) using the following primer pairs: hERα-5', CATCTGGGATGGCCCTACTGCA (SEQ ID NO:18), hERα-3' CATACTTCCCTTGTCATTGG-TACTGGCCA (SEQ ID NO:19); hERβ-5' AACTTG-GAAGGTGGGCCTGGT (SEQ ID NO:20), hERβ-3' ACCATTCCCACTTCGTAACACTTCCGAA (SEQ ID NO:21); hERβcx2-5' CAGCCTGTTCGACCAAGTGC (SEQ ID NO:22) and hERβcx2-3' GTTAAACTCTCTGC-GACAGTGCCATAGAC (SEQ ID NO:23).

Aliquots of the PCR reactions were analyzed at 30 cycles prior to the amplification plateau and again at 35 cycles (FIG. 6).

Example 7

Functional Characterization of ERβcx2

Cell Culture and Transient Transfection

The estrogen response element (ERE) containing reporter, ERα, and ERβ expression plasmids have been described previously (Bodine, et al J Cell Biochem 1997; 65: 368-387 and Bhat et al. J Steroid Biochem Mol Biol 1998; 67(3): 233-40). The ERβcx2 expression plasmid was constructed by cloning a BstXI/XbaI fragment of the original ERβcx2 clone (ef1-3/pCR 2.1) into the ERβ expression plasmid digested with the same restriction enzymes. The sequence of the clone was confirmed by sequence analysis. An SV40-β gal plasmid (Promega, Madison, Wis.) was used to normalize transfections.

Cells were transfected with lipofectamine 2000 and incubated in the presence or absence of estrogen for 24 hrs. Luciferase expression was monitored in the cell lysates. Transient transfections were performed in HepG2 cells maintained in DMEM supplemented with 10% fetal bovine serum. Twenty-four hours prior to transfection, cells are seeded in phenol red-free (PRF) DMEM containing 10% charcoal-stripped serum (csFBS), into collagen-coated 6 well plates (Biocoat, Becton Dickenson). Cells ($6\times10^5$) were transfected with 2-4 μg of receptor or reporter plasmids using Lipofectamine or Lipofectamine 2000 reagent with OPTI-MEM media according to the manufacturer's protocols (Invitrogen, Carlsbad, Calif.). After 6 hrs, the medium was replaced with 10% csFBS in PRF DMEM containing $10^{-6}$ μM 17b-estradiol (E2) or ethanol vehicle. 24 hrs later, cells were and luciferase activity was quantitated in an automated ML 1000 Luminometer (Dynex Technologies, Chantilly, Va.,). β-galactosidase activity was measured in cell lysates to normalize for differences in transfection efficiency. Preparative transfections for Western analysis were performed in 100 mm dishes and required volumes and masses to be multiplied by a factor of 6.

To define the potential functional properties of the ERβcx2 isoform, in vitro assays were performed utilizing expression plasmids for various estrogen receptor isoforms and an ERE-tk reporter construct. In a representative experiment (FIG. 7), ligand-activated transcription of the ERE-reporter was induced 23-fold by ERα. The ERβ expression construct activated transcription 8.0 fold upon stimulation with E2. ERβ is be a weak transcriptional activator and consistently shows lower efficiency compared with ERβ activity in these assays. By contrast in these same experiments, luciferase activity was unchanged for the DNA construct expressing ERβcx2 and the negative control pcDNA3.0. Thus it appears that, substitution of the c-terminal sequence in ERβcx2 disrupts the LBD and generates, not unexpectedly, an isoform functionally inactive for transactivation from a traditional estrogen receptor response element.

ImmunoBlot Analysis of Transiently Expressed ERα, ERβ, and ERβcx2

To confirm that protein was being expressed from the ERβcx2 DNA construct, immunoblot analysis was performed on cell lysates from duplicate transfections.

Samples of whole cell lysates (generally 10-25 mg protein) were mixed with 2×SDS loading buffer denatured and electrophoresed on 10-20% SDS polyacrylamide gradient gels. Separated proteins were transferred to PVDF membranes (NOVEX) for immunodetection with the ECL detection system (Amersham Pharmacia Biotech, Piscataway, N.J.). A polyclonal anti-human ERα antibody; HC-20 (Panvera, Madison, Wis.), was used to detect the ERα isoform. ERβ and the ERβcx2 fusion were revealed with EF-304 polyclonal (WO99/07847) (LBD; amino acids 247-530). The ERβcx2 fusion is detected by this polyclonal ERβ antibody despite containing only a portion of the LBD (amino acids 247-469).

The immunoblot assays were performed briefly as follows. PAGE gels were electro-blotted (Biorad, Hercules, Calif.) and the filters were blocked for 2 hrs with 5% dry milk in PBS+0.3% Tween (PBS-T). A 1:1000 (ERβ) or 1:4000 (ERβ) dilution of the primary antibody was added to the 5% dry milk in PBS-T for 2-18 hours. Following 3×10 min PBS-T washes, the primary staining was detected by incubating the filter with a 1:3000 dilution of donkey anti-rabbit horseradish peroxidase-conjugated IgG for 1 hr in PBS-T. Following 3×PBS-T washes, filters were developed with the ECL substrate as recommended (Amersham Pharmacia Biotech, Piscataway, N.J.)and the blots were exposed to Hyperfilm-MP (Amersham Pharmacia Biotech, Piscataway, N.J.).

The polyclonal antibody specific for ERα recognized a single band of appropriate MW (65 Kd) in both the transfected cells and for the recombinant ERα positive control (FIG. 8, panel A). The second antibody developed to the LBD of ERβ (amino acids 247-530) visualized ERβ in the transfected cells as well as the recombinant protein. The recombinant beta protein was significantly overloaded and the higher MW band potentially represents aggregated protein in this analysis. ERβcx2 which is truncated in the LBD, was nonetheless recognized by the ERβ polyclonal as a protein of an appropriately smaller size in transfected cell lysates (FIG. 8, panel B). Furthermore, since it is likely that not all the epitopes exist in the truncated variant, the signal intensity for transiently expressed ERβcx2 relative to ERβ may be diminished. The data suggests that the ERβcx2 protein is expressed in our transfection experiments.

ERβcx2 Isoform Shows Dominant Negative Activity.

Cotransfection experiments were performed to demonstrate potential dominant negative effects of the ERβcx2 variant on estrogen signaling. In these experiments, the ERE-tk reporter was cotransfected with either ERα or ERβ and increasing amounts of the ERβcx2 expression plasmid. Luciferase acitivity was measured in 48 hrs. As shown in FIG. 9, ERα induces transcription maximally with E2 ligand activation. As increasing amounts of the ERβcx2 expression construct are added luciferase activity is diminished. Cotransfection experiments performed with ERβ expression plasmid demonstrate a similar dominant negative effect on the ERβ signaling pathway. As shown in FIG. 10, ERβ induces transcription maximally with E2 ligand activation and as increasing amounts of the ERβcx2 expression construct are added, signaling through ERβ is reduced. In summary therefore, ERβcx2 appears to have the potential to inhibit both ER signaling pathways, possibly by the generation of transcriptionally inactive ER's through a non-productive heterodimerization mechanism. In contrast to the previously published ERβcx, which showed significant dominant negative activity against ERα transactivation only, ERβcx2 demonstrates activity for both isoforms potentially. These studies provide the first evidence of a dominant negative regulator of the ERβ isoform specifically.

What is claimed is:

1. An isolated nucleic acid fragment encoding an estrogen receptor variant polypeptide selected from the group consisting of:
   (a) an isolated nucleic acid fragment encoding SEQ ID NO:1;
   (b) an isolated nucleic acid fragment encoding an amino acid sequence having at least 95% identity with the SEQ ID NO:1, wherein the amino acid sequence has dominant-negative estrogen receptor activity;
   (c) an isolated nucleic acid molecule that hybridizes with the isolated nucleic acid fragment of (a) under hybridization conditions of 6×SSC (1M NaCl), 45% to 50% formamide, 1% SDS at 37° C., and a wash in 0.5× to 1×SSC at 55° C. to 60° C., wherein the complement of the isolated nucleic acid fragment encodes an amino acid sequence that has dominant-negative estrogen receptor activity; and
   (d) an isolated nucleic acid fragment that is complementary to (a), (b) or (c).

2. An isolated nucleic acid fragment of claim 1(a), wherein the isolated nucleic acid fragment is SEQ ID NO:2.

3. An isolated nucleic acid fragment of claim 1, wherein the isolated nucleic acid fragment is a DNA sequence.

4. The isolated nucleic acid fragment of claim 1, wherein the isolated nucleic acid fragment is an RNA sequence.

5. A nucleic acid fragment of claim 1(b), wherein the nucleic acid fragment comprises SEQ ID NO:4.

6. The nucleic acid fragment of claim 1, wherein the nucleic acid fragment encodes a polypeptide that is an estrogen signaling pathway polypeptide.

7. A chimeric construct comprising the isolated nucleic acid fragment of any of claims 1, 2, or 5 operatively linked to a regulatory sequence.

8. A host cell transformed with the chimeric construct of claim 7.

9. The host cell of claim 8, wherein the host cell is selected from the group consisting of an eukaryotic cell, a prokaryotic cell, and a cell from a multicellular organism.

10. The host cell of claim 8, wherein the host cell is a mammalian cell.

11. The host cell of claim 8, wherein the host cell is selected from the group consisting of a human hepatoma cell (HepG2), a chinese hamster ovary cell (CHO), a monkey COS-1 cell line, a mammalian cell CV-1, an amphibian cell, a yeast cell, and an insect cell.

12. The host cell of claim 8 wherein, the host cell is selected from the group consisting of a *Saccharomyces cerevisiae* cell, a *Schizosaccharomyces pombe* cell, and a *Pichia pastoris* cell.

13. A vector comprising the nucleic acid fragment of claim 1.

14. The vector of claim 13, wherein the vector is a plasmid.

15. The vector of claim 14, wherein the plasmid is pERβcx2.

16. A transformed cell comprising the vector of claim 13.

17. The transformed cell of claim 16 wherein the transformed cell is of human hepatoma cell (HepG2) origin, Chinese hamster ovary cell (CHO) origin, monkey COS-1 cell line origin, mammalian cell CV-1 origin, amphibian cell origin, yeast cell origin, or insect cell origin.

18. The transformed cell of claim 16, wherein the transformed cell is a *Saccharomyces cerevisiae*, a *Schizosaccharomyces pombe*, a *Pichia pastoris*.

19. The transformed cell of claim 16, wherein the host microorganism is *E. coli*.

20. An isolated nucleic acid fragment selected from the group consisting of:
  (a) an isolated nucleic acid fragment as set forth in SEQ ID NO:11;
  (b) an isolated nucleic acid molecule that hybridizes with the isolated nucleic acid fragment of (a) under hybridization conditions of 6×SSC (1M NaCl), 45 to 50% formamide, 1% SDS at 37° C., and a wash in 0.5× to 1×SSC at 55 to 60° C., wherein the isolated nucleic acid molecule that hybridizes with the isolated nucleic acid fragment of (a) encodes an amino acid sequence that has dominant-negative estrogen receptor activity; and
  (c) an isolated nucleic acid fragment that is complementary to (a), or (b).

21. The isolated nucleic acid fragment of claim 1, wherein the estrogen receptor variant polypeptide does not comprise the C terminal 61 amino acids of the estrogen beta receptor.

* * * * *